United States Patent [19]

Wuelknitz et al.

[11] Patent Number: 5,182,101
[45] Date of Patent: Jan. 26, 1993

[54] ANTI-PLAQUE TOOTHPASTE

[75] Inventors: Peter Wuelknitz, Langenfeld-Berghausen; Rudolf Lehmann, Leichlingen; Hans-Juergen Klueppel, Duesseldorf, all of Fed. Rep. of Germany

[73] Assignee: Henkel Kommanditgesellschaft auf Aktien, Duesseldorf-Holthausen, Fed. Rep. of Germany

[21] Appl. No.: 835,965

[22] PCT Filed: Aug. 16, 1990

[86] PCT No.: PCT/EP90/01345
§ 371 Date: Feb. 20, 1992
§ 102(e) Date: Feb. 20, 1992

[87] PCT Pub. No.: WO91/02511
PCT Pub. Date: Mar. 7, 1991

[30] Foreign Application Priority Data

Aug. 24, 1989 [DE] Fed. Rep. of Germany ....... 3927982

[51] Int. Cl.$^5$ .......................... A61K 7/16; A61K 7/22
[52] U.S. Cl. ........................................ 424/54; 424/49
[58] Field of Search ..................................... 424/49–58

[56] References Cited

U.S. PATENT DOCUMENTS

| | | | |
|---|---|---|---|
| 4,042,678 | 8/1977 | Gaffar | 424/54 |
| 4,080,441 | 3/1978 | Gaffar | 424/54 |
| 4,098,880 | 7/1978 | Gaffar | 424/54 |
| 4,100,270 | 7/1978 | Gaffar | 424/54 |
| 4,102,993 | 7/1978 | Gaffar | 424/54 |
| 4,110,429 | 8/1978 | Gaffar et al. | 424/54 |
| 4,241,049 | 12/1980 | Colodney | 424/54 |
| 4,339,430 | 7/1982 | Gaffar | 424/54 |
| 4,748,158 | 5/1988 | Biermann et al. | 424/54 |
| 4,820,507 | 4/1989 | Kluppel et al. | 424/54 |
| 5,078,988 | 1/1992 | Lin et al. | 424/54 |

FOREIGN PATENT DOCUMENTS

| | | |
|---|---|---|
| 414128 | 2/1991 | European Pat. Off. . |
| 3345781 | 6/1985 | Fed. Rep. of Germany . |
| 3444958 | 6/1986 | Fed. Rep. of Germany . |
| 3927982 | 2/1991 | Fed. Rep. of Germany . |
| 2341302 | 10/1977 | France . |
| 9102511 | 3/1991 | PCT Int'l Appl. . |

Primary Examiner—Shep K. Rose
Attorney, Agent, or Firm—Ernest G. Szoke; Wayne C. Jaeschke; Norvell E. Wisdom, Jr.

[57] ABSTRACT

Toothpastes which contain 10–60 wt. % of polishing agents, 2–20 wt. % of humectants, 0.5–5 wt. % of water-soluble consistency regulators and 0.05–0.5 wt. % of antimicrobial biguanides, as well as 1–5 wt. % of other additives from the group of surface-active substances, aromatic oils, and sweeteners, have a particularly high biguanide availability if the polishing agent consists mainly of calcium carbonate, the consistency regulators are non-ionic polysaccharide derivatives and the surface-active substances are cationic surfactants with a linear alkyl group containing 12–18 carbon atoms and one or two tertiary amino groups or quaternary ammonium groups. Optionally a non-ionogenic solubilizer for the aromatic oil may also be present in the toothpastes.

16 Claims, No Drawings

ANTI-PLAQUE TOOTHPASTE

BACKGROUND OF THE INVENTION

1. Field of the Invention

This invention relates to a toothpaste in the form of a dispersion of calcium carbonate as polish in an aqueous carrier which contains an antimicrobial biguanide compound as plaque-inhibiting component and of which the other components are selected according to type and quantity so that plaque formation is optimally inhibited despite a relatively low dosage of the antimicrobial biguanide compound.

2. Statement of Related Art

It has long been known that antimicrobial biguanide compounds are effective in preventing the formation of dental plaque. However, their effect is greatly reduced or even completely eliminated by many of the components typically used in toothpastes, more particularly by certain polishes, such as calcium carbonate for example, and also by many binders and viscosity regulators, surfactants and even by certain sweeteners. Accordingly, there has been no shortage of attempts to find components which do not impair antimicrobial biguanides or which prevent any such impairment. Thus, according to DE-OS 21 58 149 for example, α-aluminum oxide trihydrate having a certain particle size is used as the polish component. On the other hand, according to DE-OS 34 44 958, certain surfactants enhance the effect of antimicrobial biguanide. However, this effect also is disturbed in the presence of calcium carbonate as polish or in the presence of anionic binders and viscosity regulators, anionic surfactants and solubilizers.

DESCRIPTION OF THE INVENTION

Summary of the Invention

Accordingly, a satisfactory toothpaste which is extremely effective in inhibiting plaque formation, even despite low doses of the antimicrobial biguanide compounds, is not known from the prior art. The problem addressed by the present invention was to solve this problem for toothpastes containing chalk as the polish component. The present invention relates to a toothpaste in the form of an aqueous dispersion containing 10 to 60% by weight of polish, 2 to 20% by weight of humectants, 0.5 to 5% by weight of water-soluble viscosity regulators, 0.05 to 0.5% by weight of antimicrobial biguanides and 1 to 5% by weight of other additives from the group of surfactants, flavoring oils and sweeteners, characterized in that calcium carbon-ate (chalk) is predominantly present as the polish, non-ionic polysaccharide derivatives are present as the viscosity regulators and a cationic surfactant containing a linear $C_{12-18}$ alkyl group and one or two tertiary amino groups or quaternary ammonium groups are present as the surfactants, a nonionic solubilizer for the flavoring oil optionally being present.

DESCRIPTION OF PREFERRED EMBODIMENTS

The polish used is preferably a precipitated chalk of which the particles are essentially smaller than 20 μm in diameter, better yet smaller than 10 μm and preferably between 1 and 5 μm.

Suitable humectants are glycerol, sorbitol, propylene glycol and polyethylene glycols, glycerol and/or sorbitol being preferred. Suitable water-soluble viscosity regulators are nonionic polysaccharide derivatives, for example methyl, hydroxyethyl and hydroxypropyl ethers of cellulose, starch, guar, xanthan and vegetable gums. Hydroxyethyl cellulose and methyl hydroxypropyl cellulose are preferably used.

The 1,1'-hexamethylene-bis-{5-(4-chlorophenyl)-biguanide} ("chlorhexidine") known from GB-A-705,838 in the form of a water-soluble, physiologically acceptable salt, for example in the form of the acetate or gluconate, is used as the antimicrobial biguanide compound. Other antimicrobial biguanide compounds suitable for the purposes of the invention are, for example, 1,1'-hexamethylene-bis-{5-(4-fluorophenyl)-biguanide} ("fluorhexidine"), the polyhexamethylene biguanide compounds of the Vantocil IB (ICI) type known from GB-A-702,268 and the antimicrobial biguanide compounds known from U.S. Pat. Nos. 2,684,924, 2,990,425, 3,468,898, 4,022,834, 4,053,636 and 4,198,392.

Preferred cationic surfactants in the toothpaste according to the invention are those corresponding to general formula I

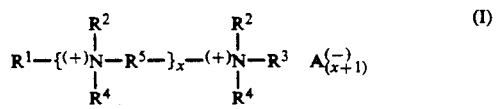

in which $R^1$ is a $C_{12-20}$ alkyl or hydroxyalkyl group, $R^2$ and $R^3$ represent a $C_{1-4}$ alkyl group or a $C_{2-4}$ 2-hydroxyalkyl group, $R^4$ is hydrogen, a $C_{1-4}$ alkyl group, a benzyl group or a $C_{2-4}$ 2-hydroxyalkyl group, $R^5$ is a $C_{1-4}$ alkylene group, $x = 0$ or $1$ and $A^{(-)}$ is a fluoride, chloride, bromide, methoxy-sulfate or ethoxysulfate anion. These cationic surfactants are present in a quantity of 0.01 to 1% by weight. Particularly suitable cationic surfactants corresponding to formula I are, for example, cetyl trimethyl ammonium chloride, lauryl dimethyl benzyl ammonium chloride, stearyl dimethyl benzyl ammonium chloride, 2-hydroxydodecyl-2-hydroxyethyl dimethyl ammonium chloride, N-octadecyl-N,N',N'-tris-(2-hydroxyethyl)-1,3-diaminopropane dihydrochloride (amine fluoride).

The addition of the cationic surfactants corresponding to general formula I to the toothpaste according to the invention significantly reduces the sorption of the antimicrobial, plaque-inhibiting biguanide compounds on the polish, so that the biguanide compound remains freely available in the toothpaste and fully available for preventing plaque. By addition of the cationic surfactants according to the invention, it is possible to produce plaque-inhibiting toothpastes containing calcium carbonate a the polish. Increasing the freely available chlorhexidine in a chalk dispersion containing 0.1% by weight chlorhexidine by addition of the cationic surfactants is demonstrated in Example 1.

The toothpaste according to the invention can be improved in its organoleptic properties by addition of flavoring oils and sweeteners. Suitable flavoring oils are any of the natural and synthetic flavorings typically used for oral and dental care preparations. Natural flavorings may be used both in the form of the ethereal oils isolated from the drugs and in the form of the individual components isolated therefrom. The toothpaste according to the invention should preferably contain at least one flavoring oil from the group consisting of peppermint oil, spearmint oil, aniseed oil, Japanese anise oil, caraway oil, eucalyptus oil, fennel oil, cinnamon oil, clove oil, geranium oil, sage oil, pimento oil, thyme oil, majoram oil, basil oil, citrus oil, gaultheria oil or one or more components of these oils either isolated therefrom or synthetically produced. The most important components of the oils mentioned are, for example, menthol, carvone, anethol, cineol, eugenol, cinnamaldehyde, caryophyllene, geraniol, citronellol, linalool, salvene, thymol, terpinene, terpineol, methyl chavicol and methyl salicylate. Other suitable flavorings are, for example, menthyl acetate, vanillin, ionone, linalyl acetate, rhodinol and piperitone.

According to the invention, a nonionic solubilizer is required for solubilizing these generally water-insoluble flavoring oils in the toothpaste. Suitable solubilizers belong to the group of surface-active compounds. Accordingly, the present invention relates to a toothpaste according to the invention containing 0.1 to 0.5% by weight of a flavoring oil and 0.1 to 0.7% by weight of a nonionic solubilizer, preferably from the group of ethoxylated fatty acid glycerides, ethoxylated fatty acid sorbitan partial esters, or fatty acid partial esters of glycerol and sorbitan ethoxylates.

Solubilizers from the group of ethoxylated fatty acid glycerides include, above all, adducts of approximately 20 to 60 moles of ethylene oxide with mono- and diglycerides of linear $C_{12-18}$ fatty acids or with triglycerides of hydroxy fatty acids, such as hydroxystearic acid or ricinoleic acid. Other suitable solubilizers are ethoxylated fatty acid sorbitan partial esters, i.e. preferably adducts of 20 to 60 moles of ethylene oxide with sorbitan monoesters and sorbitan diesters of $C_{12-18}$ fatty acids. Other suitable solubilizers are fatty acid partial esters of glycerol and sorbitan ethoxylates, i.e. preferably mono- and di-esters of $C_{12-18}$ fatty acids and adducts of 20 to 60 moles of ethylene oxide with 1 mole of glycerol or 1 mole of sorbitol.

The toothpaste according to the invention preferably contains adducts of 20 to 60 moles of ethylene oxide with hydrogenated or non-hydrogenated castor oil (i.e. with hydroxystearic acid or ricinoleic acid triglyceride), with glycerol mono- and/or di-stearate, or with sorbitan mono- and/or di-stearate as solubilizers for any flavoring oils present.

Suitable sweeteners are either natural sugars, for example sucrose, maltose, lactose and fructose, or synthetic sweeteners, but preferably nonionic or amphoteric substances. The preferred sweetener is L-aspartyl-L-phenyl alanine methyl ester commercially available as Aspartame ®.

Other known toothpaste additives may also be present in small quantities of, in all, up to at most 3% by weight providing they are compatible with the antimicrobial biguanide and do not impair its effect. Such additives are, for example, caries inhibitors, such as sodium fluoride or sodium monofluorophosphate, pigments, such as titanium dioxide for example dyes, pH regulators and buffers, for example citric acid and salts thereof or phosphoric acid and alkali metal salts thereof, and wound-healing and anti-inflammatory agents, such as for example allantoin, urea, azulene or camomile-based active substances.

The following Examples are intended to illustrate the invention without limiting it in any way.

EXAMPLES

1. Testing of the Increase in the Content of Freely Available Analytically Detectable Chlorhexidine After Addition of Cationic Surfactant A standard dispersion of 40% by weight chalk (calcium carbonate) and 0.1% by weight chlorhexidine in water was prepared and increasing quantities of cationic surfactants were added. After addition of the cationic surfactant, the dispersions were shaken for 24 hours to establish the equilibrium position at 20° C. The dispersions were then diluted with 3 parts by weight of water per part by weight of dispersion, filtered off from the calcium carbonate and tested for the free chlorhexidine content in the clear filtrate. The free chlorhexidine was analytically determined by the method described by Cropper, Platt and Puttnam in *J. Soc. Cosmet. Chem.* 26, (1975), pages 355-373.

The following cationic surfactants were used:
A: Cetyl trimethyl ammonium bromide
B: 2-Hydroxydodecyl-2-hydroxyethyl dimethyl ammonium chloride
C: N-octadecyl-N,N',N'-tris-(2-hydroxyethyl)-1,3-diaminopropane dihydrofluoride (so-called amine fluoride).

The type and concentration of cationic surfactant added and the quantity of freely available chlorhexidine, after 24 hours of equilibration, in % of the quantity added are shown in the following Table.

|  | Example No. | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| Cation. surfactant | — | A | A | A | A | B | B | B | B | C | C | C |
| Concentration % by weight | — | 0.01 | 0.05 | 0.1 | 0.5 | 0.01 | 0.05 | 0.1 | 0.5 | 0.17 | 0.33 | 0.66 |
| Free chlorhexidine in % | 15 | 15 | 27 | 64 | 90 | 20 | 20 | 20 | 33 | 20 | 20 | 85 |

2. Toothpaste According to the Invention

| Formulation: | |
|---|---|
| Chalk (precipitated calcium carbonate) | 40.0% by weight |
| Sorbitol (70% solution) | 5.0% by weight |
| Glycerol | 5.0% by weight |
| Methyl hydroxypropyl cellulose[1] | 2.5% by weight |
| Hydroxyethyl cellulose[2] | 1.3% by weight |
| Cation. surfactant C (amine fluoride) | 1.0% by weight |
| Peppermint flavoring oil | 0.3% by weight |
| HR 60[3] | 0.3% by weight |
| Chlorhexidine digluconate | 0.2% by weight |
| Aspartame ® | 0.01% by weight |
| Water | ad 100% by weight |

[1] The commercial product Culminal MHPC 100 (Henkel KGaA) was used.
[2] The commercial product Cellobond HEC (BP) was used.
[3] Adduct of 60 moles of ethylene oxide with hydrogenated castor oil.

What is claimed is:

1. A toothpaste in the form of an aqueous dispersion containing 10.0 to 60.0% by weight of polishes, 2.0 to 20.0% by weight of humectants, 0.5 to 5.0% by weight of water-soluble viscosity regulators, 0.05 to 0.5% by weight of antimicrobial biguanides, and 1.0 to 5.0% by weight of other additives from the group of surfactants, flavoring oils, and sweeteners, wherein the improvement is that calcium carbonate is predominantly present as the polish, non-ionic polysaccharide derivatives are present as the viscosity regulators, and a cationic surfactant containing a linear $C_{12}$-alkyl group and one or two tertiary amino groups or quaternary ammonium groups is present as the surfactant, a nonionic solubilizer for the flavoring oil optionally being present.

2. A toothpaste as claimed in claim 1, wherein 1,1'-hexamethylene-bis-(4-chlorophenyl)-biguanide (chlorhexidine) in the form of a water-soluble salt is present as the antimicrobial biguanide.

3. A toothpaste as claimed in claim 2, wherein a cationic surfactant corresponding to formula (I)

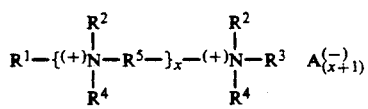

in which $R^1$ is a $C_{12-20}$ alkyl or hydroxyalkyl group; $R^2$ and $R^3$ represent a $C_{1-4}$ alkyl group or a $C_{2-4}$ 2-hydroxyalkyl group; $R^4$ is hydrogen, a $C_{1-4}$ alkyl group, a benzyl group, or a $C_{2-4}$ 2-hydroxyalkyl group; $R^5$ is a $C_{1-4}$ alkylene group; $x=0$ or 1; and $A^{(-)}$ is a fluoride, chloride, bromide, methoxysulfate, or ethoxysulfate anion, is present as the cationic surfactant in a quantity of 0.01 to 1% by weight.

4. A toothpaste as claimed in claim 3, which contains 0.1 to 0.5% by weight of a flavoring oil and 0.1 to 0.7% by weight of a solubilizer from the group of ethoxylated fatty acid glycerides, ethoxylated fatty acid sorbitan partial esters or fatty acid partial esters of glycerol or sorbitan ethoxylates.

5. A toothpaste as claimed in claim 4, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

6. A toothpaste as claimed in claim 1, wherein a cationic surfactant corresponding to formula (I)

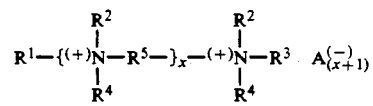

in which $R^1$ is a $C_{12-20}$ alkyl or hydroxyalkyl group; $R^2$ and $R^3$ represent a $C_{1-4}$ alkyl group or a $C_{2-4}$ 2-hydroxyalkyl group; $R^4$ is hydrogen, a $C_{1-4}$ alkyl group, a benzyl group, or a $C_{2-4}$ 2-hydroxyalkyl group; $R^5$ is a $C_{1-4}$ alkylene group; $x=0$ or 1; and $A^{(-)}$ is a fluoride, chloride, bromide, methoxysulfate, or ethoxysulfate anion, is present as the cationic surfactant in a quantity of 0.01 to 1% by weight.

7. A toothpaste as claimed in claim 6, which contains 0.1 to 0.5% by weight of a flavoring oil and 0.1 to 0.7% by weight of a solubilizer from the group of ethoxylated fatty acid glycerides, ethoxylated fatty acid sorbitan partial esters, or fatty acid partial esters of glycerol or sorbitan ethoxylates.

8. A toothpaste as claimed in claim 2, which contains 0.1 to 0.5% by weight of a flavoring oil and 0.1 to 0.7% by weight of a solubilizer from the group of ethoxylated fatty acid glycerides, ethoxylated fatty acid sorbitan partial esters, or fatty acid partial esters of glycerol or sorbitan ethoxylates.

9. A toothpaste as claimed in claim 1, which contains 0.1 to 0.5% by weight of a flavoring oil and 0.1 to 0.7% by weight of a solubilizer from the group of ethoxylated fatty acid glycerides, ethoxylated fatty acid sorbitan partial esters, or fatty acid partial esters of glycerol or sorbitan ethoxylates.

10. A toothpaste as claimed in claim 9, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

11. A toothpaste as claimed in claim 8, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

12. A toothpaste as claimed in claim 7, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

13. A toothpaste as claimed in claim 6, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

14. A toothpaste as claimed in claim 3, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

15. A toothpaste as claimed in claim 2, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

16. A toothpaste as claimed in claim 1, wherein an adduct of 20 to 60 moles of ethylene oxide with a material selected from the group consisting of hydrogenated and non-hydrogenated castor oil, glycerol mono- and di-stearate and mixtures of mono- and di-stearate, and sorbitan mono- and di-stearate and mixtures of mono- and di-stearate is present as the solubilizer for the flavoring oil.

* * * * *

UNITED STATES PATENT AND TRADEMARK OFFICE
CERTIFICATE OF CORRECTION

PATENT NO. : 5,182,101

DATED : Jan. 26, 1993

INVENTOR(S) : Wuelknitz et al.

It is certified that error appears in the above-identified patent and that said Letters Patent is hereby corrected as shown below:

In claim 1, column 5, line 3, "$C_{12}$" should read -- $C_{12-18}$ --.

Signed and Sealed this

Eighth Day of February, 1994

Attest:

BRUCE LEHMAN

Attesting Officer        Commissioner of Patents and Trademarks